United States Patent [19]

Averback

[11] Patent Number: 4,919,915
[45] Date of Patent: Apr. 24, 1990

[54] METHOD FOR DETECTING THE ABILITY TO PREVENT RED-TO-GREEN CONGOPHILIC BIREFRINGENCE

[76] Inventor: Paul Averback, 180, 4$^e$ Rang, St. Liguori, Quebec, Canada, J0K 2X0

[21] Appl. No.: 315,796

[22] Filed: Feb. 27, 1989

Related U.S. Application Data

[63] Continuation-in-part of Ser. No. 21,242, Mar. 3, 1987, Pat. No. 4,816,416, which is a continuation-in-part of Ser. No. 901,007, Aug. 27, 1986, abandoned.

[51] Int. Cl.$^5$ ............................................. G01N 21/78
[52] U.S. Cl. ........................................ 424/7.1; 424/9; 435/4; 436/2; 436/164; 436/174; 436/177; 436/183; 436/811
[58] Field of Search .................... 436/2, 164, 166, 183, 436/172, 811, 174, 177, 178; 424/7.1, 9; 435/4

[56] References Cited

U.S. PATENT DOCUMENTS 4,666,829  5/1987  Glenner et al. .................... 436/63 X

OTHER PUBLICATIONS

Averback, *Acta Neuropathol.* 61: 148–152 (1983).
Hara, *J. Neuropath. Exp. Neurol.* (1986).
Selkoe et al., *Science* 235: 873 (1987).
Graves & Kickhan, *New England J. Med.* 214: 782–783 (1936).
Wallace, *The Lancet* (Feb. 20, 1932), at 391–393.
Kennet et al., *Curr. Top. Microbiol. Immunol.* 81: 77–91 (1978).
Wisniewski et al., *J. Neuropathol. & Exp. Neurol.* 32: 566 (1973).

*Primary Examiner*—Robert J. Hill, Jr.
*Attorney, Agent, or Firm*—Foley & Lardner, Schwartz, Jeffery, Schwaab, Mack, Blumenthal & Evans

[57] ABSTRACT

A method for detecting the ability of a compound to prevent development of red-to-green congophilic birefringence. The method is carried out by contacting the compound with dense microspheres which are derived from mammalian brain tissue and which, when disrupted, display red-to-green congophilic birefringence upon staining with Congo Red dye under conditions such that said dense microspheres are disrupted. Thereafter the disrupted dense microspheres are stained with Congo Red dye and any development of red-to-green congophilic birefringence in the stained disrupted dense microspheres is detected.

13 Claims, 1 Drawing Sheet

METHOD FOR DETECTING THE ABILITY TO PREVENT RED-TO-GREEN CONGOPHILIC BIREFRINGENCE

This is a continuation-in-part application bases on Ser. No. 07/021,242, filed Mar. 3, 1987, now U.S. Pat. No. 4,816,416 which is a continuation-in-part application bases on Ser. No. 06/901,007, filed Aug. 27, 1986, now abandoned. The respective disclosures of these earlier-filed applications are incorporated herein by reference.

BACKGROUND OF THE INVENTION

The present invention relates to the identification of compounds that act, at physiologically-compatible levels, to inhibit the formation of proteinaceous tissue deposits denoted generally as "amyloid". More specifically, the present invention relates to pharmaceutically active agents that impede formation of amyloid fibrils in vivo, and to a method for the screening of compounds which posses this activity.

Classified under the rubric "amyloidosis" are a number of pathological conditions characterized by the deposition of abnormal fibrils ("amyloid fibrils") in extracellular spaces. The amyloid fibril, in turn, represents a final common pathway for a diverse array of proteins. Regardless of their biochemical composition, however, all types of amyloid fibrils share (a) a β-pleated sheet structure, (b) green birefringence under polarized light after staining with Congo Red dye, and (c) a fibrillar morphology which has a typical electron-microscopic appearance.

The deposition of amyloid fibrils can affect several organs in the systemic forms of the disorder, exemplified by familial Mediterranean fever, familial amyloid polyneuropathy and systemic amyloidosis, or it can be restricted to one organ in localized forms. Among the latter are conditions classified under the rubric "cerebral amyloidosis," which covers the Alzheimer group of diseases, namely, Alzheimer's disease [pre-senile dementia, senile dementia]; Alzheimer's disease associated with Down's syndrome; Alzheimer's disease associated with other central-nervous-system diseases, such as Parkinson's disorder; and congophilic angiopathy [associated or not associated with Alzheimer's disease].

There is no effective therapy for cerebral amyloidosis, which almost invariably has a fatal outcome following the onset of amyloid deposits. For example, Alzheimer's disease is estimated to be the fourth or fifth leading cause of death among North Americans.

A universally accepted indicator of cerebral amyloidosis is the accumulation of large numbers of lesions, so-called "senile plaques", that are comprised in large part of amyloid fibrils. Senile plaques are spherical, ranging from 10 to 200 μm in diameter, and are found occasionally in aged adult cerebral cortex but in large numbers in Alzheimer-affected cortex.

The utilizing of materials found in human brain (normal of Alzheimer-affected) that are not already amyloid, and of transforming them into amyloid, has not been documented in the literature. There was also no description in the art of an experimental system, derived exclusively from human materials, that was characterized by the feature of Alzheimer's disease. Because the presence of amyloid is the most qualitatively and quantitatively specific indication of senile-plaque formation, most specialists agree that reproduction of amyloid fibrils experimentally from precursor materials which are extracted, activated, or otherwise derived from human brain would constitute the best available evidence linking an agent or precursor to the progression of cerebral amyloidosis.

Despite the recognized importance of an experimental system that would permit testing for such a linkage, it has been possible to reproduce amyloid experimentally from materials derived solely from human brain tissue. Accordingly, there has been no reliable indicator available for compounds that might be effective in treating cerebral amyloidosis; nor has it been possible to determine whether a group of compounds exists that block the conversion of a brain-localized precursor to cerebral amyloid (i.e., that display "anti-amyloid activity") at physiologically acceptable levels of the active agent.

A microscopic structure referred to as the dense microsphere is known to exist in normal brain and in brain affected by Alzheimer's disease. See Averback, *Acta Neuropathol.* 61: 148–52 (1983); results confirmed by Hara, *J. Neuropath. Exp. Neurol.* (1986). Evidence for the existence of DMS comes from microscopic histological section studies of fixed whole brain tissue, where the dense microspheres are seen to have a proteinaceous central region ("DMS protein") surround by continuous membrane ("DMS membrane"). The dense microspheres are observed as randomly dispersed, very infrequent structures which occupy an estimated $10^{-9}$ or leas or total brain volume, at a unit frequency roughly estimated at $10^{-16}$ or less, relative to other definable brain structure such as mitochondria.

Neither the extraction, purification and characterization of isolated samples of DMS nor the use of DMS material to any advantage has been documented. Thus, DMS are structures of unproven function and unknown significance or usefulness, and have been effectively unavailable in tangible form.

SUMMARY OF THE INVENTION

It is therefore an object of the present invention to provide a method for the screening of therapies for usefulness in impeding amyloid formation and, hence, in treating cerebral amyloidosis, that is characterized by the presence abnormal amounts of amyloid β-protein.

It is also an object of the present invention to provide a method of treating β-amyloid diseases by the administration of a compound selected from a class of pharmaceutically active agents that have in common an ability to inhibit, at physiologically-acceptable levels, the formation of amyloid fibrils in vivo.

It is yet another object of the present invention to provide antibodies that can be used to detect the presence of DMS in biological samples.

In accomplishing the foregoing objects, there has been provided, in accordance with one aspect of the present invention, a method for screening for an ability to impede amyloid formation, comprising the steps of (i) disrupting dense microspheres derived from mammalian brain tissue such that a material is produced that is stainable with Congo Red stain; (ii) contacting the material with Congo Red stain; and then (iii) subjecting the material to examination to detect development of congophilic birefringence. In a preferred embodiment, the screening method of the present invention further comprises the step, prior to step (i), of contacting the dense microspheres with a pharmacological agent.

In accordance with another aspect of the present invention, a method has also been provided for treating cerebral amyloidosis, comprising the step of administering to a subject, in whom amyloid formation is anticipated, a pharamaceutically effective amount of a compound that inhibits formation of amyloid fibrils when administered, at an in-tissue concentration of about $10^{-5}$M or less, to a test animal that has received an intracerebral injection of DMS. In one preferred embodiment, the compound thus administered inhibits amyloid formation by acting on DMS protein or DMS membrane in such a way that a structural transition of DMS protein in situ to a β-pleated sheet conformation is prevented.

In accordance with yet another aspect of the present invention, a composition of matter has been provided consisting essentially of antibodies, preferably monoclonal antibodies, that are reactive against dense microspheres derived from mammalian brain tissue.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has now been discovered that the development of amyloid fibrils associated, for example, with the evolution of cerebral amyloidosis is tied to the unchecked disruption of DMS in vivo. The connection between DMS disruption and amyloid formation is evidenced in part by the fact that disrupted DMS treated with Congo Red stain display a red-green congophilic birefringence identical to that found in senile-plaque amyloid. Thus, the most significant aspect of the brain damage which characterizes cerebral amyloidosis can be reproduced using material derived, pursuant to the present invention, from normal mammalian brain samples.

It has also been discovered that compounds which are effective, at an in-tissue concentration of about $10^{-5}$M or less, in impeding the formation of amyloid fibrils in test animals which receive DMS via intracerebral injection can be used to treat cerebral amyloidosis, including Alzheimer's disease. Particularly effective in this regard are compounds that act on DMS protein or DMS membrane, for example, via intracellular or extracellular binding, so as to prevent a structural transition of DMS protein in situ to a β-pleated sheet conformation.

The microspheric bodies employed according to the present invention are derived from mammalian brain tissue and are characterized, in essentially homogeneous purified form, by a range of diameters from about 0.1 μm to about 15 μm, by the above-mentioned outer membrane/proteinaceous core structure of DMS and by certain stainability properties. For example, the microspheric bodies of the present invention are homogeneously electron-dense when stained with osmium and lead, and can be visualized by thin-section electron microscopy; under optical microscopic examination, they appear eosinophilic and phloxinophilic, and are nonbirefringent when stained with Congo Red. When the microspheric bodies of the present invention are disrupted, a material is produced that displays congophilic birefringence; that is, when stained with Congo Red the material becomes optically anisotropic to the extent of splitting an incident light wave into two waves with mutually perpendicular vibrational planes.

Figure 1:
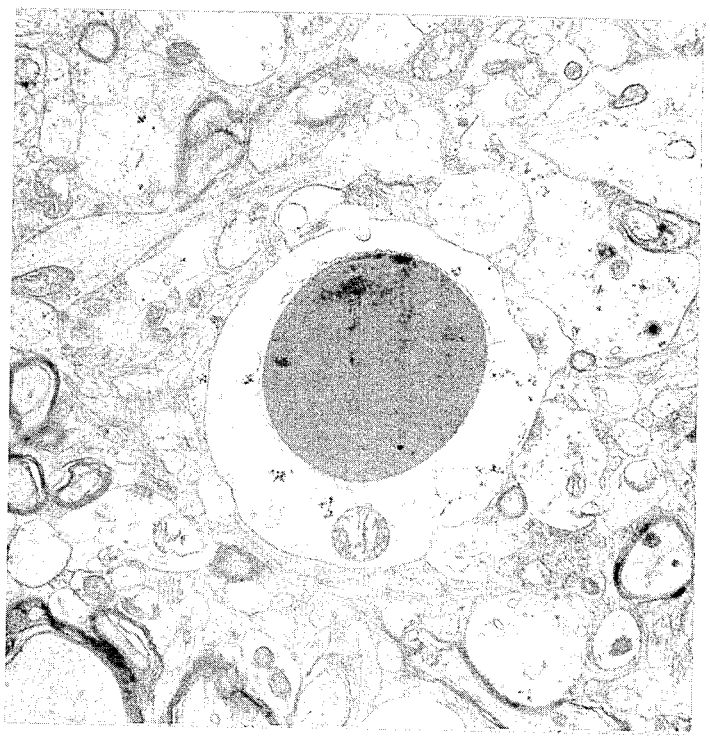
FIG. 1 is a micrographic representation of a DMS.
Figure 2:
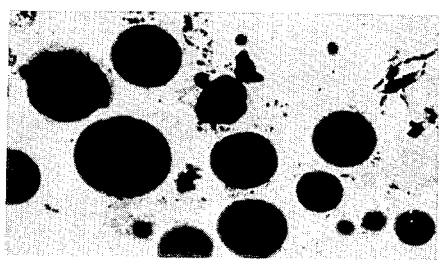
FIG. 2 is another micrographic representation showing DMS mounted on a slide in homogeneous purified form.

As shown in FIG. 1, DMS are spherical, membrane-bounded, intracellular structures, about 0.1 to 15 μm in diameter, that are found in human and other mammalian brains. Homogeneous structures of DMS in purified form can be derived by extraction of give tangible samples of homogeneous globular bodies.

The following procedure can be followed to extract DMS from brain tissue:

(1) Whole brain in removed from the skull postmortem, by use of standard postmortem techniques for humans or animals. The best results are obtained if the organism has been in circulatory arrest for less than six hours at the time of brain removal and if the body has been refrigerated as early as possible postmortem. DMS are still extractable at postmortem intervals greater than six hours and are still extractable if body cooling has been delayed or absent, but these two factors will usually greatly decrease the overall average yield of DMS per individual brain. In addition to the effects of post-circulatory arrest interval and temperature on DMS yield, there is considerable individual variation in DMS content per brain, and also individual variation in DMS extractability, which may be related to agonal metabolic state, overall disease status or other factors. All of the factors which determine total DMS yield per brain can have an impact on DMS extraction, since the volume of purified sample of homogeneous DMS will decrease proportionally to any reduction in percentage extractability; such a decrease may be sufficient to hinder accurate recognition during the extraction procedure. Furthermore, the screening of putative anti-amyloidosis therapies and the characterization of isolated samples of DMS, in accordance with the present invention, are rendered correspondingly more difficult and costly, and ultimately may be impossible at critically small volumes of DMS.

(2) By means of clean instruments, the freshly removed brain is immediately dissected. Dissection is optimally performed in a cold room at 10° C. By means of careful, but rapid, sharp and blunt dissection, the internal capsules, corona radiata, centra semi-ovale, brain stem, cerebellum, lepto and pachymeninges, arachnoid granulations, choroid plexi, and blood vessels are separated and discarded, and the remaining mass of brain is rapidly used for the subsequent steps. (Standard blocks for microscopic study can be removed at this stage and stored separately in histological fixative.) The dissected brain mass ("DBM") is optimally utilized immediately after dissection. It may also be stored frozen at temperatures of −10° C. to −70° C., but this decreases the overall average yield of DMS per individual brain.

(3) The extraction of DMS material from DBM can be carried out by a combination of centrifugation steps. In an exemplarly extraction, DBM mechanically homogenized in a 2:1 volume of 0.5M TRIS-HCL buffer (ph 7.5) is subjected to centrifugation at about 200 rpm for some 10 minutes. (All manipulations are carried out at around 4° C.) The sediment thus obtained ("Sediment I") is separated across a sucrose gradient (1.589M, or 45%; 1.895M, or 52%; 2.3895M, or 62.5%) via centrifugation at 26,000 rpm for 30 minutes. It has been found that the material that settles at the interface between 1.895M and 2.1015M (56.7% sucrose) is the DMS-containing fraction, as may be confirmed by microscopic examination, with eosin staining, of the fraction.

The DMS-containing fraction obtained from Sediment I consists essentially of the dense microspheres described above, and can be used in a screening method according to the present invention. It is preferable, however, for the fraction to be subjected to additional manipulations in order to enrich the DMS concentration. To this end, it has proved useful, for example, to wash the DMS-containing fraction in buffer—the above-mentioned homogenization buffer is suitable for this purpose—and to spin the resulting mixture again (10,000 rpm for 7 minutes) to obtain DMS-enriched sediment ("Sediment II").

As with Sediment I, Sediment II can be run through a density gradient to enrich further the yield of DMS. It has been discovered that the carbohydrate Percoll® (Pharmacia) is particularly useful in this context. A commercially available formulation of 80% Percoll® (1.13 g/ml) in 0.15M NaCl provides an iso-osmolar gradient to which Sediment II can be subjected (30,000 rpm for 15 minutes); successive samples, say, on the order of 0.25 to 1 cc each, can then be taken along the length of the gradient and the DMS-enriched fractions isolated. After these fractions are washed again in buffer, they can be spun down once again (15,000 rpm for 10 minutes) to obtain a sediment ("Sediment III") that is substantially pure DMS.

The DMS materials obtained as described above can be used, pursuant to the present invention, in screening anti-amyloidosis therapies. In particular, purified DMS material within the present invention can be employed to ascertain effectiveness in vitro, on the part of an active agent or a treatment comprising a putative therapy for cerebral amyloidosis, in preventing the red-to-green congophilic birefringence that has been found to accompany formation of amyloid when DMS are disrupted.

By whatever means DMS are disrupted in control samples, a putative anti-amyloidosis agent or therapy can be screened by virtue of its ability to retard or preclude amyloid formation under test conditions. For example, in vitro DMS disruption on an appropriate viewing surface, such as a glass or plastic slide (see Test 1 below), can be accomplished by mechanical means; by the action of an enzyme treatment, as in a 10% trypsin or pepsin solution, or other chemical exposure; or by exposing DMS material to extreme pH values (at room temperature, pH2 or pH10) or temperatures (e.g., 100° C. for one hour). Disruption of DMS can also be effected by injecting DMS material of the present invention into an isolated tissue sample (see Test 2). Brain slices are preferred for this purpose, but liver, pancreas and other organs are also acceptable sources for tissue samples.

An active agent or a treatment that proves effective in vitro is then tested, pursuant to the present invention, for in vivo efficacy in blocking amyloid-fibril formation in an animal model for cerebral amyloidosis comprised, for example, of a rat, dog, cat or other suitable laboratory animal that has been injected with purified DMS material, pursuant to the present invention. Although intracerebral injection is preferred, injection sites in a test animal's body other than in the brain, such as in skin and in muscle, are suitable for determining the ability of a proposed active agent or treatment step to hinder the resulting formation of amyloid. Because simple injection of DMS onto a glass slide does not result in amyloid formation, it is understood that in vivo production of amyloid fibrils upon injection of DMS occurs in the extracellular spaces of the injected tissue.

According to the present invention, an active agent that impedes in vivo formation of amyloid in DMS-injected test animals, when the agent is present at in-tissue concentrations of $10^{-5}$M or less, is recognized to be useful in the above-mentioned method of treating cerebral amyloidosis, including Alzheimer's disease. As a further refinement, substances falling within this newly-defined category of pharmaceutically active agents—that is, the class of compounds that, at $\leqq 10^{-5}$M concentration levels in tissues, inhibit induced amyloid formation—can be tested, pursuant to the present invention, in a second in vivo assay. Particularly preferred for this purpose is the "senile animal" model for cerebral amyloidosis, where animals such as aged dogs or monkeys, which are known to develop variable numbers of Alzheimer-type cerebral senile plaques, see Wisniewski et al, *J. Neuropathol. & Exp. Neurol.* 32: 566 (1973); Selkoe et al, *Science* 235: 873 (1987), are tested for amyloid inhibition. This in vivo assay involves initial pretreatment- and control-biopsy monitoring to confirm and quantify the presence of senile plaque, and serial cerebral biopsy to monitor quantitatively the evolution of DMS and senile plaque in situ and the presence (or absence) of amyloid-formation inhibition.

The method of the present invention for treating cerebral amyloidosis is used with subjects in whom amyloid formation is anticipated. In particular, the treatment can be applied to those who are at risk of developing cerebral amyloid, as in senile plaques, including the elderly, nondemented population and patients with the diagnoses listed above under the cerebral-amyloidosis rubric. Compounds within the present invention that display anti-amyloid activity at an in-tissue concentration of about $10^{-5}$M or less, e.g., between about $10^{-5}$ and $10^{-6}$M, can be administered to such subjects orally, rectally, via a nasal route, parenterally (including by skin or other routes), in spray or aresol form, or via inhalation. In this regard, a compound within the present invention can be administered in a physiologically-acceptable carrier therefor, such as physiological saline solution.

Determining a pharmaceutically-effective amount of a compound administered in accordance with the present invention entails standard evaluations of pharmacokinetic data and clinical efficacy. See, e.g., GOOD AND GILMAN'S THE PHARMACOLOGICAL BASIS FOR THERAPEUTICS (7th ed.). Thus, the above-described in vivo animal testing will provide the basis for a range of dosages and dosage schedules to be assessed clinically in humans. An assessment in this regard would generate pharmacokinetic data, for example, regarding bioavailability, absorption, metabolism, serum levels and excretion. Such data would be evaluated against clinical data obtained concurrently from neurobehavioral testing, for example, memory testing and testing of cognitive function, and from clinical medical assessment. If a dosage halts progression of deterioration in clinical parameters for a symptomatic patient, i.e., a subject diagnosed as suffering from cerebral amyloidosis, that dosage should also have a prophylactic effect in the elderly, nondemented population.

The following test paradigms illustrate ways in which DMS material, as described above, can be employed routinely, according to the present invention, in identifying anti-amyloidosis agents within the aforementioned class of compounds.

TEST 1

In Vitro Disruption of DMS on a Glass Slide.

Homogeneous DMS preparations are placed by droplet on a clean dry glass slide. The volume and number of DMS used is optional but is recommended to be at least several thousand to facilitate interpretation (see Example 1 below). Larger samples are more costly but are easier and more unequivocal to examine. The DMS are mechanically disrupted using a stainless steel spatula scraping and pressing the DMS against a glass slide in repetitive manual back and forth motions for one minute.

The slide is allowed to air dry. A few drops of Congo Red stain are then added to the dried slide and gently passed over the dried disrupted DMS for 30 seconds and the stain is then drained off the slide onto tissue paper or filter paper. The slide is then examined in the light microscope, the latter fitted with crossed polarizing lenses to asses red-green congophilic birefringence. The result is an unequivocal red-to-green ("apple green") birefringence similar to the red-to-apple green birefringence found in the senile-plaque amyloid of Alzheimer patients, and in quantities proportional to the volume of DMS applied to the slide initially. All other reactions, staining results, or quantitatively insignificant results are considered negative in the absence of the characteristic color change-positive staining result, in quantity proportional to the volume of DMS applied, which indicates that disrupted DMS are of the nature of senile-plaque amyloid.

For test purposes, a corresponding DMS sample is contacted with a possible pharmacological agent, and the DMS disruption/staining procedure as described above is repeated. Many variations are possible, e.g., the active agent may be applied to the DMS in solution, before application to the slide, or to the DMS on the slide. In any event, if the agent prevents the red-green birefringence observed in the negative control slide (no agent present), then the active agent should be tested further for efficacy against cerebral amyloidosis.

As a positive control, the test slide can also be compared to a slide upon which DMS were disrupted after contact with a 1% aqueous solution of sodium diphenyl-diazo-bis-α-naphthylamine sulfonate, $C_{32}H_{22}N_6Na_2O_6S_2$; the compound, Congo Red, is described by Graves & Kickham, *New England J. Med.* 214: 782–83 (1936), and Wallace, *The Lancet* (Feb. 20, 1932), at 391–93, and has been found to block amyloid formation in a microsphere-based, in vitro assay according to the present invention.

TEST 2

In Vitro Distruption of DMS in a Human Brain Slice.

Human brain postmortem samples of histological block size (block size is elective; usually 1-5 cm×1-5 cm×1-3 mm) are removed, by sterile techniques, with the aid of sterile gloves, scalpel and forceps, and then are placed in sterile empty plastic containers, such as a Petri dish before extracted DMS are injected into each brain sample at room temperature. After one hour incubation at room temperature, the brain samples are immersed in histological fixative and processed for histology by techniques that are standard for optical microscopy. Controls, size of inoculum, preparations of slides and interpretation of results are covered under discussion of in vivo Test 3 below.

TEST 3

Formation of Amyloid Induced in Vivo by Injection of DMS into Live Tissue.

Laboratory rodents are anesthetized and their brains immobilized by routine methods, and injections of purified DMS are made into superficial cerebral cortex regions through sterile needles inserted through the skull and meninges. (Sham control injections of DMS negative material can be put into either the contralateral cortex or into separate animals.) The method of anesthesia, type of craniotomy, site of injections in the brain parenchyma, size of needle and syringe or other vehicle, would closure technique, and numbers of animals used are not crucial to the test and will vary depending on the animal used. Thus, a small mouse may not need a skull flap whereas a larger mammal may need a burr hole; size of needles or vehicles may vary with animal brain size, etc. (see Example 1). The size of injection is elective: smaller injections are more difficult and costly to trace histologically (see below), but larger injections are more costly in terms of number of DMS used. An exemplary protocol is detailed in Example 1.

The animal is painlessly sacrificed about 30 minutes or more after injection. The exact time of sacrifice is elective: generally 1–24 hours is preferable, but the DMS transformation will persist and can be recognized at many time intervals. After sacrifice the brain is removed by standard methods and immersion fixed in histological fixative. Perfusion fixation is not recommended because perfusion pressures will usually disrupt the injection cavity and render the results inaccessible.

According to standard methods, the brain is fixed in toto for several days (correspondingly longer for larger animal brains), sliced, embedded, cut, mounted and stained for histological study. A dissecting microscope is used to locate the injection site and accurately place it in the block, and sections are carefully inspected during microtomy to ensure that the injection site is in the section and not discarded during trimming. The mounted slides are stained with Congo Red according to standard methodology. The sections are examined with the optical microscope fitted with polarizing lenses as above and assessed as described above with regard to the in vivo test.

The use of positive and negative controls, and the testing of putative active agents, are carried out in a manner analogous to that followed in the in vitro tests described above. Variations are possible by virtue of the fact that compounds can be tested in vivo, via injection, ingestion or other routes, before, after or during the introduction of DMS, and concurrently with or separately from the DMS. In addition, therapeutic strategies other than those based on the action of a pharmacological agent can be studied in whole animals.

By means of the foregoing tests, nontoxic compounds suitable for clinical testing in human beings can be identified, pursuant to the present invention, that impede amyloid formation, preferably by inhibiting the transition of DMS protein to a β-pleated sheet conformation. Because it is immunogenic in standard laboratory animals, the DMS material of the present invention can also used to produce polyclonal and monoclonal antibodies against dense microspheres. These antibodies, in turn, can be employed in ELISA-type assays, see, e.g., VOLLER et al, THE ENZYME LINKED IMMUNOSORBENT ASSAY (ELISA) (Dynatech Laboratories 1979), and other immunological tests, such as radioimmunoassays, for detecting DMS in biological samples. Via conventional techniques, as described, for example, by Kennet et al, *Curr. Top. Microbiol. Immunol.* 81: 77–91 (1978), anti-DMS antibodies can be produced using the DMS material of the present invention and then "tagged" with a radionuclide, a colorimetric agent or a fluorescent marker. The tagged antibodies can be used in diagnostic tests to detect the presence of components of the dense microspheres with which the antibodies react, rendering the components of the microspheres visualizable.

Other details of the present invention are further described by reference to the following illustrative examples.

EXAMPLE 1

Screening of Acetylcholine for Anti-Amyloid Activity in Vitro.

Approximately 80,000 homogeneously extracted DMS were placed in a droplet from a Pasteur pipette onto a glass slide, and the droplet was air dried. The DMS adhered to the glass slide. Acetycholine (20 mM) in physiological saline was added in a droplet, as a possible test compound, to DMS.

The DMS were mechanically disrupted, in the presence of the test compound, as described above and then were allowed to air dry. A control slide was treated exactly in the same manner, except that the test compound was not added. Congo Red stain was added, and the reaction products were examined, as previously described.

Under optical-microscopic examination with a polarizing lens, both slides showed abundant reddish stained material, respectively, in quantities of the order of magnitude as in the initial DMS droplet quantity. The reddish material was observed to turn a brilliant apple green during rotation of the polarizing lens. Rotation of the polarizing lenses back and forth demonstrated unequivocal and abundant red-to-green and green-to-red birefringence which persisted indefinitely. That both slides showed these indistinguishable results meant that acetycholine had tested negative and, hence, need not be tested further, as described above, to determine whether it belonged to the class of compounds displaying anti-amyloid activity at physiolgically-acceptable levels.

EXAMPLE 2

Compounds Identified, Via an in Vivo Assay, as Effective Amyloid-Formation Inhibitors at Physiologically-Compatible Concentrations.

IN VIVO ASSAY: Male Wistar rats of three-months age were anesthetized by ether inhalation. Their heads are immobilized by means of a stereo-tactic head brace. Bilateral parieto-occipital scalp incisions (1 cm) were made with a sterile scalpel blade. Bilateral parieto-occipital 0.5 mm burr holes are made with a 0.5 mm drill.

For each compound to be assayed (see below), six rats were each injected on one side, through the burr hole from a sterile 1 cc syringe fitted with a sterile 22 gauge needle, with sterile physiological saline containing about 400,000 human DMS and the compound (total volume: 100 μL). The injection was made into the cerebral cortex to a depth of a few millimeters, so that the injection was within the parenchyma, not on the surface or in the ventricles. Consequently, the in-tissue concentration of the compound at the site of injection corresponded to the concentration of the compound in the saline (see tabulated data below).

On the contralateral side, each of the six test rats also received an injection of sterile physiological saline (100 μL). In addition to this internal control, a control group of six rats that did not receive any injection was associated with each test group.

After injection of the test animals, a sterile suture was placed through the scalp incision to cover the wound, and the animals were observed. At post-injection intervals of one hour, twelve hours and twenty-four hours, respectively, four animals (two from the test group and two controls) were painlessly sacrificed by ether inhalation and $CO_2$ insufflation. Their brains were removed and fixed via immersion for twenty-four hours in 10% formalin. The fixed tissue was then sliced coronally, in sections of between 0.5 mm and 1 mm in thickness, and the areas of injection were dissected out and blocked as described above under "Test 3."

The blocks with the injection site were sectioned at a thickness of 6 μm, and every tenth section was mounted to provide a total of ten technically intact sections containing the injection site. The mounted sections were processed and stained with Congo Red, as previously described, and examined, via optical microscopy, with and without polarized illumination. The following measurements were made by means of an optical micrometer and standard counting grids and graticules: (1) total lesion area; (2) total number of foci of congophilic-birefringent amyloid deposits; and (3) percentage of lesion area composed of congophilic-birefringent amyloid deposits.

TESTED COMPOUNDS: An in vitro assay corresponding to Test 1, as described above, indicated that each of the following compounds possessed anti-amyloid activity at a concentration of about $10^{-2}M$.

(A) Pyrimethamine ("Daraprim")—This compound is conventionally used in the prophylaxis of malaria, and acts by inhibiting dihydrofolate reductase of the malarial plasmodia at a concentration well below the level that inhibits the mammalian enzyme. It is completely absorbed orally and is often used with other drugs in combination therapy. No effects on the central nervous system have been reported for pyrimethamine.

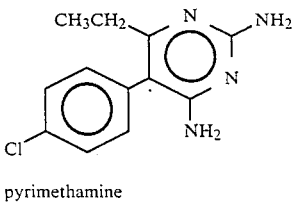

pyrimethamine (B) Dipyridamole ("Persantine")—The compound, formally designated 2,6-bis-(diethanolamino)-4,8-dipiperidinopyrimido-(5,4-)-pyrimidine, is a vasodilator by virtue of its inhibiting the uptake of adenosine by smooth muscle cells. It has no known central-nervous effects.

(C) Nifedipine ("Procardia")—Conventionally employed in cardiac therapy, nifedipine is a dihydropyridine calcium channel blocker that is rapidly and completely absorbed by sublingual administration. It is 98% bound to plasma proteins, and vasodilation is its only major toxic effect. There are not known effects on the central nervous system for this drug.

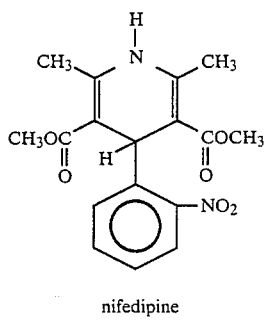

nifedipine (D) Cromolyn Sodium ("Intal")—The known uses of this compound trace to its activity in preventing the release of histamine and other agonists in asthmatic or allergic reactions. It is poorly absorbed orally, with about 10% entering the lungs when the compound is administered, as a powder, from an inhaler. There are no known central-nervous effects.

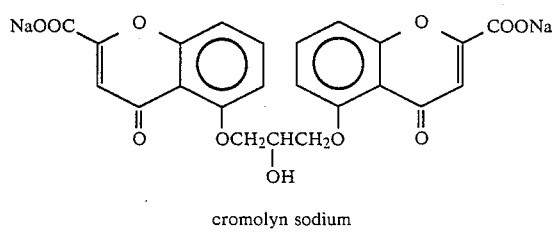

cromolyn sodium (E) Congo Red (sodium diphenyldiazo-bis-α-naphthylamine sulfonate)—The compound is a dye that has been used as a pH indicator and as a histologic stain, as well as for determination of blood volume and for other diagnostic tests. For example, it is injected intravenously in a test for amyloidosis, whereby 30% of the dye disappears from the blood of a normal person within an hour but 40% to 100% disappears over the same period from a the blood of a victim of amyloid disease. It has heretofore had no recognized biological activity per se, however.

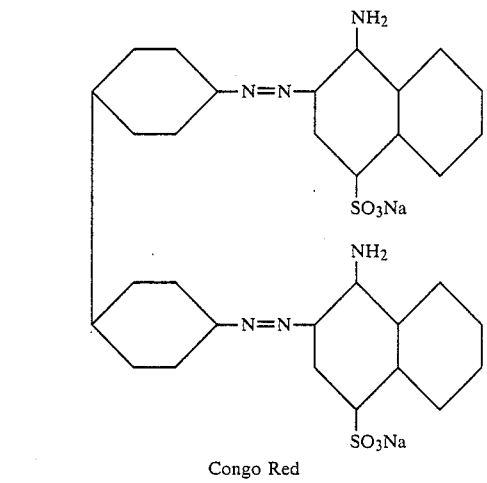

Congo Red (F) Sulfisoxazole ("Gantrisin")—The compound has a good antibacterial spectrum, and is rapidly absorbed and excreted. It binds plasma proteins. Sulfisoxazole has no known effects on the central nervous system, other than antibacterial.

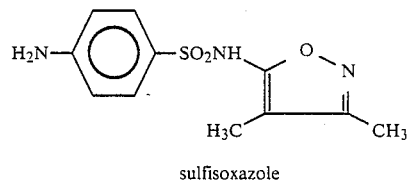

sulfisoxazole (G) Erythromycin—A water-soluble, orally effective antibiotic of the macrolide family, erythromycin inhibits protein synthesis by binding to 50S ribosomal subunits of sensitive microorganisms. It is absorbed by the small intestine and has a half-life of about sixteen hours. The compound has no known central-nervous effects.

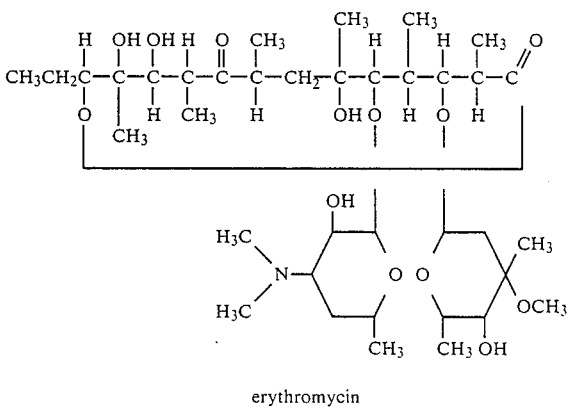

erythromycin

RESULTS: Standard tests for statistically significant differences of means were applied to the above-mentioned measurement data, generated from the brain sections for the six test groups (one group per tested compound) and the corresponding control groups. As shown in the following table, each of the tested compounds effected a significant reduction at $10^{-2}$M ($p<0.01$). But only three compounds, pyrimethamine, cromolyn sodium and erythromycin, were found to inhibit amyloid formation in vivo at in-tissue levels in the range of $10^{-5}$ to $10^{-6}$M and, hence, to fall in the category of substances suitable for the treatment method of the present invention.

TABLE

| Compound | Mean Lesion Area Examined [mm²] | | Mean Number of CBADs* Per Animal | | Mean Lesion Area Composed of CBADs* | |
|---|---|---|---|---|---|---|
| | ($10^{-5}$–$10^{-6}$ M) | ($10^{-2}$ M) | ($10^{-5}$–$10^{-6}$ M) | ($10^{-2}$ M) | ($10^{-5}$–$10^{-6}$ M) | ($10^{-2}$ M) |
| Daraprim | 10.1 | | 4 | | 0.2** | |
| erythromycin | 12.8 | | 2 | | 0.2** | |
| Intal | 8.9 | | 2 | | 0.4** | |
| Gantrisin | 10.4 | 10.8 | 1 | 108 | 0.1** | 8.4 |
| Persantine | 11.0 | 9.4 | 4 | 146 | 0.2** | 14.6 |
| Procardia | 13.2 | 9.8 | 4 | 88 | 0.2** | 7.6 |
| Congo Red | 12.4 | 10.4 | 1 | 104 | 0.1** | 8.0 |
| <untreated> | | 11.2 | | 132 | | 8.2 |
| | | [S.D.1.2] | | [S.D. 12] | | [S.D. 0.2] |

*Congophilic Birefringent Amyloid Deposits
**Significant decrease from untreated controls ($p < 0.001$)

What is claimed is:

1. A method for detecting the ability of a compound to prevent red-to-green congophilic birefringence as a possible indication of the compound's ability to impede amyloid formation comprising the steps of
   (i) contacting a compound with a reagent in a first sample, wherein the reagent consists essentially of dense microspheres which are derived from mammalian brain tissue and which, when disrupted, display red-to-green congophilic birefringence upon standing with Congo Red dye, under conditions such that said dense microspheres are disrupted in said first sample; thereafter
   (ii) staining a test material selected from the group consisting of the first sample or a portion thereof which contains at least some of the disrupted dense microspheres with Congo Red dye; and
   (iii) detecting any development of red-to-green congophilic birefringence in the stained test material.

2. The method according to claim 1 which further comprises
   (iv) comparing any detected development of red-to-green congophilic birefringence of step (iii) with any detected development of red-to-green congophilic birefringence obtained by carrying out said disrupting, staining, and detecting with reagent which has not been contacted with said compound.

3. The method according to claim 1 which further comprises
   (iv) comparing any detected development of red-to-green congophilic birefringence of step (iii) with any detected development of red-to-green congophilic birefringence obtained by carrying out said disrupting, staining, and detecting with reagent which has been contacted with a 1% aqueous solution of Congo Red dye.

4. The method according to claim 1, wherein said first sample comprises tissue into which each of said reagent and said compound is introduced.

5. The method according to claim 4, wherein each of said reagent and said compound is introduced in vivo.

6. The method according to claim 5, wherein said tissue is brain tissue.

7. The method according to claim 4, wherein said compound is introduced in vivo into an animal and said reagent is introduced in vitro into a tissue sample isolated from said animal.

8. The method according to claim 7, wherein said tissue is brain tissue.

9. The method according to claim 1, wherein step (i) includes introducing said reagent onto a glass or plastic surface before disruption thereon of said dense microspheres.

10. The method according to claim 9, wherein said disruption is effected mechanically.

11. The method according to claim 9, wherein said disruption is effected by subjecting said dense microspheres to an enzymatic treatment.

12. The method according to claim 9, wherein said disruption is effected by exposing said dense microspheres to pH conditions sufficient to disrupt said dense microspheres.

13. The method according to claim 9, wherein said disruption is effected by exposing said dense microspheres to temperature conditions sufficient to disrupt said dense microspheres.

* * * * *